(12) United States Patent
Paufique

(10) Patent No.: US 7,815,948 B2
(45) Date of Patent: Oct. 19, 2010

(54) METHOD OF OBTAINING A FIRMING ACTIVE PRINCIPLE, ACTIVE PRINCIPLE THUS OBTAINED AND USES THEREOF

(75) Inventor: Jean Paufique, Objat (FR)

(73) Assignee: Societe Industrielle Limousine d'Application Biologique SILAB, Objat (FR)

( * ) Notice: Subject to any disclaimer, the term of this patent is extended or adjusted under 35 U.S.C. 154(b) by 695 days.

(21) Appl. No.: 11/661,808

(22) PCT Filed: Aug. 25, 2005

(86) PCT No.: PCT/FR2005/050685

§ 371 (c)(1),
(2), (4) Date: May 31, 2007

(87) PCT Pub. No.: WO2006/027521

PCT Pub. Date: Mar. 16, 2006

(65) Prior Publication Data

US 2008/0038388 A1    Feb. 14, 2008

(30) Foreign Application Priority Data

Sep. 1, 2004    (FR) .................................. 04 51951

(51) Int. Cl.
*A61K 36/42* (2006.01)
(52) U.S. Cl. ...................................................... 424/758
(58) Field of Classification Search ...................... None
See application file for complete search history.

(56) References Cited

U.S. PATENT DOCUMENTS

| | | | |
|---|---|---|---|
| 4,464,296 A * | 8/1984 | Jacks et al. .................. | 530/377 |
| 5,547,673 A | 8/1996 | Bombardelli et al. | |
| 5,660,850 A * | 8/1997 | Boss, Jr. ...................... | 424/426 |

FOREIGN PATENT DOCUMENTS

| | | |
|---|---|---|
| FR | 2 791 255 | 9/2000 |
| FR | 2 832 418 | 5/2003 |
| FR | 2 849 776 | 7/2004 |
| WO | WO 02/102347 | 12/2002 |

* cited by examiner

*Primary Examiner*—Christopher R. Tate
*Assistant Examiner*—Deborah A. Davis
(74) *Attorney, Agent, or Firm*—Young & Thompson

(57) ABSTRACT

The invention relates to a method of obtaining a firming active principle resulting from the solubilization of *Cucurbita pepo* seed meal treated by means of enzymatic hydrolysis. The invention also relates to the active principle thus obtained and to the uses thereof in cosmetics.

14 Claims, No Drawings

METHOD OF OBTAINING A FIRMING ACTIVE PRINCIPLE, ACTIVE PRINCIPLE THUS OBTAINED AND USES THEREOF

This invention relates to a process for obtaining a firming active ingredient from *Cucurbita pepo* seed meal that is able to fight against deformations of the dermis such as stretch marks or wrinkles.

The invention also covers the active ingredient that is obtained and the functionalities.

Simple chronological aging causes alterations of the characteristics of the extracellular matrix that consists of collagen fibers and elastic fibers. These fibers, however, have a very low renewal rate in adults.

The collagen fibers represent the majority of the total mass of the dermis. This collagen network makes it possible to give rise to a functional tissue that ensures the holding of the superficial layers of the skin. The collagens of types I, III and V are primarily concerned.

It is therefore advisable to find substances that can preserve the essential elasticity of the skin and that can therefore preserve the network of elastic fibers and collagen. It is also known that to preserve this asset, it is also necessary to fight against the consequences of other phenomena that are likely to cause profound alterations, such as puberty, pregnancy, modifications of a hormonal nature or skin treatments.

Thus, the object of this invention is to select a natural active ingredient by a suitable process that makes it possible to promote the synthesis of certain molecules and to limit the action of certain enzymes.

Thus, it is known that, in the family of metalloproteinases:
- The MMP-1, or collagenase-1, degrade the collagens of types I, II and III,
- The MMP-2 or gelatinase A play an important role in the final degradation of the collagen fibers but also in the hydrolysis of the elastin.

Another enzyme, the cathepsin L, causes a significant alteration of the elastic network and also degrades the collagens.

The invention is now described in detail, first through its process for obtaining the firming active ingredient, with an anti-stretch mark and anti-wrinkle aim, then through the suitable characteristics of the active ingredient that is obtained, and finally through the mechanisms that are involved, through results that are obtained by in-vitro and in-vivo tests.

1/PRODUCTION PROCESS

The process according to the invention comprises the following stages:
- Solubilization of the *Cucurbita pepo* seed meal in an aqueous solution at a rate of at least 50 g/l,
- Simultaneous or successive enzymatic hydrolysis(es),
- Separation of the soluble and insoluble phases by any suitable means, in particular by centrifuging,
- Inactivation of the enzymatic activities,
- Mechanical filtration, and
- Successive concentrations of the active fraction followed by a sterilizing filtration.

*Cucurbita pepo* is a plant of the cucurbit family.

2/CHARACTERIZATION OF THE ACTIVE INGREDIENT OBTAINED FROM CUCURBITA PEPO

2-1/Level of Dry Material:

The level of dry material is obtained by passage of a given amount of active ingredient that is obtained by the implementation of the process, placed in the oven at 105° C. until a constant weight is achieved.

The level of dry material for the active ingredient according to the invention is between 20 and 200 g/l, more particularly between 50 and 70 g/l.

2-2/Measurement of pH:

The pH is measured by the potentiometric method at ambient temperature. The pH values of the active ingredient according to the invention are between 5 and 9, more particularly between 6.5 and 7.5.

2-3/Determination of the Nitrogen Content:

The determination is made by the LOWRY method.

The derived protein content, regardless of the protein source, is between 15 and 145 g/l, more particularly between 38 and 50 g/l.

2-4/Characterization of the Protein Fraction:

The distribution of the molecular weights of the different molecular radicals that are present in the active ingredient, obtained by the implementation of the process according to the invention, is determined by FPLC (Fast Protein Liquid Chromatography).

Markers allow use as standards, and it is noted that the protein fraction has a molecular weight of less than 40,000 Daltons.

2-5/Characterization of Carbohydrates:

2-5-1/Metering of Simple Sugars:

The level of simple sugars is divided into 54.5% of glucose and 45.5% of fructose.

2-5-2/Degree of Polymerization

The table below shows that the glucidic fraction of the active ingredient according to this invention comprises glucose and fructose in the form of oligosaccharides and polysaccharides with a degree of polymerization that is greater than or equal to 7.

|  | Degree of Polymerization | Level of Carbohydrates |
|---|---|---|
| Monosaccharides | 1 | 3.7% |
| Disaccharides | 2 | 7.9% |
| Oligosaccharides | 3 | 1.3% |
| Oligosaccharides | 4 | 3.5% |
| Oligosaccharides | 5 | 0.9% |
| Oligosaccharides | 6 | 0.4% |
| Oligo- and Polysaccharides | $\geq 7$ | 82.3% |

2-6/Identification of the Active Fraction:

To carry out this identification, the active ingredient is studied in its complete composition, referred to as PA, and the active ingredient of which one molecular fraction was precipitated by a lowering of the pH, referred to as $PA_5$.

2-6-1/Comparative Analysis:

The efficacies of the two products are compared relative to their activities with regard to the synthesis of the MMP-1 in the normal human fibroblast cultures, subjected to UVA irradiation.

The study is carried out by Western Blot.

|  | Level of MMP-1 | Level of MMP-1/Irradiated Control |
|---|---|---|
| Non-Irradiated Control | 100% | — |
| Irradiated Control | 223% | — |
| PA at 2% + UVA | 123% | −81 |
| $PA_5$ at 2% + UVA | 225% | 0 |

The active ingredient makes it possible to limit the synthesis of the MMP-1 while the active ingredient that is reduced by one fraction does not make it possible to obtain this limitation.

This fraction is therefore the active fraction.

2-6-2/Determination of the Active Fraction:

The LOWRY method is used again, and the protein contents for PA and $PA_5$ are compared.

It is noted that 19% of the proteins disappeared during the lowering of the pH to 5.0.

|  | Proteins/Dry Material | Variation |
|---|---|---|
| PA | 78% | — |
| $PA_5$ | 63% | −19% |

A molecular analysis by liquid gel-filtration chromatography indicates that the protein fraction has a molecular weight of 29,000 Daltons.

2-7/Stability—Solubility:

The active ingredient PA in aqueous solution is stable:
For pH values located between 2.0 and 10.0,
At a temperature of between 40 and 80° C.,
In ethanol, in mixtures that contain at most 40% of pure ethanol.

The active ingredient is stable in various cosmetic formulations. Thus, the active ingredient is introduced at 5% in the following formulas:

Clear gel with a base of carbopol, phenonip and water,
Opaque gel with a base of Sepigel 305, phenonip and water,
Emulsified gel with a base of Montanov 202, isopropyl palmitate, phenonip, Sepigel 305 and water,
Anionic emulsion with a base of stearic acid, triethanolamine, isopropyl palmitate, phenonip and water,
Cationic emulsion with a base of quaternium-82, cethyl alcohol, isopropyl palmitate, phenonip and water, or else
Non-ionic emulsion with a base of Montanov 202, simulsol 165, isopropyl palmitate, phenonip and water.

The active ingredient according to the invention is also stable with regard to the raw materials that are used in cosmetics such as thickeners, emulsifiers or alcoholic solvents up to 40%.

3/IN-VITRO TESTS OF EFFICACY 3-1/Studies of the Capacity of the Active Ingredient to Limit the Degradation of the Cutaneous Fibers.

The studies are conducted on human fibroblasts that are obtained from stretch marks and normal human fibroblasts.

The active ingredient is used at a concentration of 2%.

3-1-1/Effect of the Active Ingredient on the Synthesis of the Cathepsin-L.

Whereby this enzyme has a high elastolytic activity in the fibroblasts, it is noted that the active ingredient according to the invention makes it possible to reduce the synthesis of this enzyme and to return to a level that is comparable to that of the normal human fibroblasts.

After incubation of the two types of fibroblasts in the culture medium that may or may not be in the presence of the active ingredient and Western Blot analysis, the following results are obtained:

|  | Level of Cathepsin-L in % |
|---|---|
| Control of Normal Fibroblasts | 100 |
| Control of Stretch Mark Fibroblasts | 128 |
| Normal Fibroblasts + 2% Active Ingredient | 98 |
| Fibroblasts of Stretch Marks + 2% Active Ingredient | 104 |

3-1-2/Effect of the Active Ingredient on the MMP-1 Synthesis.

The MMP-1 metalloprotease, responsible for the degradation of the collagen fibers I and III, should see its synthesis reduced in the presence of the active ingredient according to this invention, and it is this that is noted in the following results, obtained in the cultures of normal human fibroblasts and fibroblasts that are obtained from stretch marks, analyzed by Western Blot.

|  | Level of MMP-1 in % |
|---|---|
| Control of Normal Fibroblasts | 100 |
| Control of Stretch Mark Fibroblasts | 168 |
| Normal Fibroblasts + 2% Active Ingredient | 103 |
| Stretch Mark Fibroblasts + 2% Active Ingredient | 101 |

3-1-3/Effect of the Active Ingredient on the Activity of the MMP-2.

The MMP-2 metalloprotease intervenes in the degradation of the collagen fibers and in the hydrolysis of the elastin. It is suitable for fighting against its activity and this analysis shows the anti-MMP-2 activity of the active ingredient according to the invention.

This analysis is conducted by zymography on cultures of normal human fibroblasts and fibroblasts that are obtained from stretch marks.

The results confirm this anti-MMP-2 activity with a reduction of 69%.

|  | Level of MMP-2 in % |
|---|---|
| Control of Normal Fibroblasts | 100 |
| Control of Stretch Mark Fibroblasts | 272 |
| Normal Fibroblasts + 2% Active Ingredient | 99 |
| Fibroblasts of Stretch Marks + 2% Active Ingredient | 153 |

3-2/Study on the Capacity of the Active Ingredient to Reorganize the Fibrous Network:

3-2-1/Effect of the Active Ingredient on the Cell Renewal:

The object is to compare the capacity for proliferation and replication of the normal human fibroblasts and that of the stretch mark fibroblasts, in the absence and in the presence of the active ingredient according to the invention.

The results are obtained by MTT spectrophotometric color measurement.

It is noted that the active ingredient according to the invention makes it possible to restore a capacity for proliferation of the fibroblasts that are obtained from stretch marks comparable to that of normal fibroblasts.

|  | Optical Density at 540 nm |
| --- | --- |
| Control of Normal Fibroblasts | 0.541 |
| Control of Stretch Mark Fibroblasts | 0.411 |
| Normal Fibroblasts + 2% Active Ingredient | 0.732 |
| Stretch Mark Fibroblasts + 2% Active Ingredient | 0.536 |

3-2-2/Effect of the Active Ingredient on the Synthesis of Collagen I:

The study is carried out by ELISA metering on normal human fibroblasts and on fibroblasts that are obtained from stretch marks.

It is noted that the active ingredient, dosed at 2%, increases significantly, 62%, the synthesis of collagen I.

|  | Collagen I Synthesis (ng/ml) | Variation of the Collagen/Control Level |
| --- | --- | --- |
| Control of Normal Fibroblasts | 130 | — |
| Control of Stretch Mark Fibroblasts | 150 | — |
| Normal Fibroblasts + 2% Active Ingredient | 202 | +55 |
| Stretch Mark Fibroblasts + 2% Active Ingredient | 243 | +62 |

3-2-3/Effect of the Active Ingredient on the Synthesis of Fibrillin:

Whereby fibrillin is a protein that is involved in the organization of the elastic fiber network, the study aims at comparing the fibrillin synthesis level in cultures of normal human fibroblasts and obtained from stretch marks.

The capacity of the active ingredient to restore this capacity of synthesis for fibroblasts obtained from stretch marks and to increase this synthesis of normal fibroblasts is noted.

|  | Level of Fibrillin |
| --- | --- |
| Control of Normal Fibroblasts | 100% |
| Control of Stretch Mark Fibroblasts | 75% |
| Normal Fibroblasts + 2% Active Ingredient | 115% |
| Stretch Mark Fibroblasts + 2% Active Ingredient | 99% |

4/IN-VIVO TESTS OF EFFICACY 4-1/Effect on the Microrelief of Stretch-Marked Skin:

Imprints are made on volunteers in determined stretch-marked zones and in non-stretch-marked zones, before and after 42 and 84 days of twice-daily counter-placebo treatments.

These imprints are analyzed by means of a profilometer that is equipped with an image analyzer.

It is possible to determine the gray levels of the digital images that are obtained.

Suitable software makes it possible to obtain mean roughness.

In this case, the active ingredient is used in formulation with the following galenical formula:

| Isopropyl palmitate: | 10% |
| --- | --- |
| Isononyl isononanoate (Lanol 99) | 8% |
| Arachidyl alcohol/behenyl alcohol/arachidyl glucoside (Montanov 202) | 5% |
| Glycerol | 3% |
| Myreth-3 Myristat (Lanol 14M) | 2% |
| Glycol palmitate (Lanol P) | 1% |
| Shea butter | 1% |
| Phenonip | 0.7% |
| Viscolam AT 64 | 0.5% |
| Active ingredient according to the invention | 4% |
| Water (sufficient quantity for) | 100% |

It is noted that the active ingredient according to the invention makes it possible to reduce significantly the differences in roughness of 14% between the stretch-marked zones and the non-stretch-marked zones.

The active ingredient makes it possible to smooth the differences between the stretch-marked zones and the non-stretch-marked zones; the stretch marks are then less visible.

PPI: Roughness with the active ingredient according to the invention.

PPL: Roughness with the placebo according to the invention.

|  | Active Ingredient ΔPPI | Placebo ΔPPL | ΔΔ |
| --- | --- | --- | --- |
| J0 | −20% | −18% | −2% |
| J42 | −13% | −18% | +5% |
| J84 | −11% | −25% | +14% |

4-2/Effect on the Biomechanical Properties of Stretch-Marked Skin:

The objective of this study is to quantify in vivo, on volunteers, the firming effect of the active ingredient that is formulated at 4% in emulsion by evaluation of the Biomechanical properties of the skin at the level of stretch marks by means of a device that is marketed under the name "cutometer."

An effort is made to measure, among the mechanical properties:

The cutaneous elasticity (the more the value of the coefficient tends toward 1 and the more elastic the skin)

The tone (the lower the value of the coefficient and the better the skin tone)

The biological deformation (the value of the parameter tends toward 1 and the more the skin deforms), and The capacity of the skin to return to its initial state (the more the value tends toward 0 and the more the skin quickly returns to its normal state).

The galenical formulation is identical to that of the preceding test.

Cutaneous Elasticity
  Pe: Cutaneous elasticity with active ingredient.
  Pi: Cutaneous elasticity with placebo.

|     | Active Ingredient ΔPe | Placebo ΔPi | ΔΔ   |
| --- | --------------------- | ----------- | ---- |
| J0  | −12%                  | −15%        | +3%  |
| J42 | −6%                   | −14%        | +8%  |
| J84 | −9%                   | −20%        | +11% |

It is noted that the variation of elasticity between the stretch-marked zones and the non-stretch-marked zones remains stable in the zone that receives the placebo and decreases in the zone that is treated with the active ingredient. This result was observed in 65% of the volunteers.

Tone
  Pe: Skin tone with active ingredient.
  Pi: Skin tone with placebo.

|     | Active Ingredient ΔPe | Placebo ΔPi | ΔΔ   |
| --- | --------------------- | ----------- | ---- |
| J0  | 21%                   | 31%         | −10% |
| J42 | 10%                   | 35%         | −25% |
| J84 | 11%                   | 36%         | −25% |

The tone difference is 25% between the two stretch-marked and non-stretch-marked zones.
This result is obtained in 70% of the volunteers.

Biological Deformation
  Pe: Cutaneous deformation with active ingredient.
  Pi: Cutaneous deformation with placebo.

|     | Active Ingredient ΔPe | Placebo ΔPi | ΔΔ   |
| --- | --------------------- | ----------- | ---- |
| J0  | 23%                   | 28%         | −5%  |
| J42 | 12%                   | 24%         | −12% |
| J84 | 13%                   | 28%         | −15% |

A reduction of 15% of the biological deformation is noted at 84 days.
This result is obtained in 65% of the volunteers.

Capacity of the Skin to Return to its Normal State
  Pe: Capacity to return to the normal state of a zone treated with the active ingredient.
  Pi: Capacity to return to the normal state of a zone treated with the placebo.

|     | Active Ingredient ΔPe | Placebo ΔPi | ΔΔ   |
| --- | --------------------- | ----------- | ---- |
| J0  | 6%                    | 19%         | −13% |
| J42 | 12%                   | 37%         | −25% |
| J84 | 10%                   | 40%         | −30% |

A reduction of 30% in the difference of return to the initial state is noted.

4-3/Effect on the Firming Properties:
Among the firming properties of the active ingredient, an attempt is made to measure:
  The crude cutaneous elasticity (the more the value of the coefficient tends toward 1 and the more elastic the skin)
  The net cutaneous elasticity (the more the value of the coefficient tends toward 1 and the more elastic the skin).
The tested galenical formulation is as follows:

| | |
| --- | --- |
| Arachidyl alcohol/behenyl alcohol/arachidyl glucoside (Montanov 202) | 5% |
| Glycol palmitate (Lanol P) | 1% |
| Myreth-3 Myristat (Lanol 14 M) | 2% |
| Isopropyl palmitate | 10% |
| Isononyl isononanoate (Lanol 99) | 8% |
| Shea butter | 1% |
| Sodium acrylate/sodium acryloyldimethyl taurate copolymer C13-14 isoparaffin/Laureth-7/sorbitan oleate (Viscolam AT 64) | 0.5% |
| Glycerol | 3% |
| Phenonip | 0.7% |
| Active ingredient | 4% |
| Water (sufficient quantity for) | 100% |

Crude Cutaneous Elasticity
  Pe: Crude elasticity with active ingredient.
  Pi: Crude elasticity with placebo.

|     | Active Ingredient Pe | Placebo Pi | ΔΔ (%) |
| --- | -------------------- | ---------- | ------ |
| J0  | 0.414                | 0.426      |        |
| J21 | 0.443                | 0.409      | 11.0%  |
| J42 | 0.488                | 0.424      | 17.4%  |

An increase in the crude elasticity in the zones treated with the active ingredient is noted relative to the zones that receive the placebo.

Net Crude Elasticity
  Pe: Net elasticity with active ingredient.
  Pi: Net elasticity with placebo.

|     | Active Ingredient Pe | Placebo Pi | ΔΔ (%) |
| --- | -------------------- | ---------- | ------ |
| J0  | 0.319                | 0.343      |        |
| J21 | 0.348                | 0.316      | 17.0%  |
| J42 | 0.419                | 0.361      | 26.1%  |

An increase in the net elasticity is noted in the zones that are treated with the active ingredient relative to the zones that receive the placebo. This result was observed in 68% of the volunteers.

4-4/Effect on the Microrelief of Normal Skin:
Imprints are made on the forearms of the volunteers, before and after 28 and 56 days of twice-daily counter-placebo treatments.
These imprints are analyzed by means of a profilometer that is equipped with an image analyzer.
It is possible to determine the gray levels of the digital images that are obtained.
Suitable software makes it possible to obtain mean roughness.
The active ingredient is used in the same galenical formula as the preceding test.

It is noted that the active ingredient according to the invention makes it possible to reduce significantly the roughness by 6% after 56 days of twice-daily treatment.

4-5/Anti-Wrinkle Effect:

The objective of this study is to quantify in vivo the anti-wrinkle efficacy of the 4%-formulated active ingredient in counter-placebo emulsion.

The test is carried out on the crows-feet of 20 healthy female volunteers of a median age of 57 years.

The anti-wrinkle effect is analyzed by observation of imprints using a profilometer that is equipped with an image analyzer that makes it possible to obtain the following parameters:

The number of wrinkles,
The total wrinkled surface area, and
The total length of the wrinkles.

In this case, the active ingredient is applied twice daily in formulation with the following galenical formula:

| | |
|---|---|
| Isononyl isononanoate (Lanol 99) | 7% |
| Arachidyl alcohol/behenyl alcohol/arachidyl glucoside (Montanov 202) | 4% |
| Cetearyl ethylhexanoate (Lanol 1688) | 3% |
| Isopropyl palmitate | 3% |
| PEG-100 stearate/glyceryl stearate (Simulsol 165) | 1% |
| Phenonip | 0.7% |
| Stearyl stearate 5Richtachol SS | 0.5% |
| Cetyl alcohol | 0.5% |
| Active ingredient according to the invention | 4% |
| Water (sufficient quantity for) | 100% |

The results that are obtained after 28 and 56 days of twice-daily application are expressed in the following table in percentage of variation relative to the results that are obtained with the placebo:

| | Number of Wrinkles (Variation/Placebo) | Total Wrinkled Surface Area (Variation/Placebo) | Total Length of the Wrinkles (Variation/Placebo) |
|---|---|---|---|
| J28 | −5% | −16% | −17% |
| J56 | −19% | −39% | −30% |

It is noted that the 4%-formulated active ingredient in emulsion according to the invention makes it possible to reduce significantly the number of wrinkles by 19%, the total wrinkled surface area by 39%, and the total length of the wrinkles by 30% after 56 days of twice-daily application.

The in-vitro tests, like the in-vivo tests, show the activities of the ingredient that is extracted from a plant of the cucurbit family, the *Cucurbita pepo*, and in particular its ability to fight against stretch marks and wrinkles and more extensively against the deformations of the dermis.

The active ingredient can be introduced into cosmetic compositions with various galenical forms, of which certain examples have been provided above in an illustrative and non-limiting way.

The galenical formulations can include creams, ointments, aqueous or alcoholic lotions, aqueous or alcoholic emulsions or gel, whereby the active ingredient concentration varies from 0.1% by weight to 10%, preferably from 2 to 4%.

The invention claimed is:

1. A method for obtaining a skin firming active ingredient comprising:
    (a) solubilizing *Cucurbita pepo* seed meal in an aqueous solution;
    (b) simultaneously or successively enzymatically hydrolyzing the solution from step (a);
    (c) separating soluble and insoluble phases of the solution from step (b);
    (d) inactivating the enzymatic activity in the soluble phase from step (c);
    (e) mechanically filtering a solution of the soluble phase from step (d);
    (f) concentrating an active fraction comprising the active ingredient from the solution of step (e); and
    (g) sterile filtering the concentrated active fraction from step (f), to obtain the active ingredient.

2. An active ingredient obtained by the method according to claim 1, having the following properties:
    a level of dry material between 20-2000 g/l;
    a pH in a range of 5.0-9.0;
    a nitrogen content between 15-145 g/l;
    a protein fraction having a molecular weight of less than 40,000 Daltons; and
    a sugar content of about 54.5% glucose and about 45.5% fructose with a degree of polymerization of more than 7.

3. The active ingredient according to claim 2, having the following properties:
    a level of dry material between 50-70 g/l;
    a pH in a range of 6.5-7.5; and
    a nitrogen content between 35-50 g/l.

4. The active ingredient according to claim 2, having a protein fraction of about 29,000 Daltons.

5. A method for limiting the degradation of cutaneous fibers, comprising applying to skin in need thereof an effective amount of the active ingredient according to claim 2.

6. The method according to claim 5, wherein the effective amount of the active ingredient limits the synthesis of cathepsin-L and reduces the synthesis of metalloproteinases MMP-1 and MMP-2.

7. A method for restoring the capacity for proliferation of fibroblasts from stretch marks, comprising applying to skin in need thereof an effective amount of the active ingredient according to claim 2.

8. The method according to claim 1, wherein the *Cucurbita pepo* seed meal is solubilized in step (a) at a rate of 50 g/l.

9. The method according to claim 1, wherein separating soluble and insoluble phases in step (c) is performed by centrifugation.

10. A method for increasing the synthesis of collagen I, comprising applying to skin in need thereof an effective amount of the active ingredient according to claim 2.

11. A method for restoring the capacity for synthesis of fibrillin in fibroblasts from stretch marks, comprising applying to skin in need thereof an effective amount of the active ingredient according to claim 2.

12. A method for reducing the roughness of stretch-marked skin comprising applying to skin in need thereof an effective amount of the active ingredient according to claim 2.

13. A method for enhancing elasticity, tone and capacity of the skin to return to its normal state, and to limit biological deformation of the skin, comprising applying to skin in need thereof an effective amount of the active ingredient according to claim 2.

14. A method for reducing the number, total surface area, and total length of wrinkles of the skin, comprising applying to skin in need thereof an effective amount of the active ingredient according to claim 2.

* * * * *